US008900194B2

(12) United States Patent
Clarke et al.

(10) Patent No.: US 8,900,194 B2
(45) Date of Patent: Dec. 2, 2014

(54) MICRONEEDLE DEVICES AND MICRONEEDLE DELIVERY APPARATUS

(75) Inventors: Graham M. Clarke, Woodbury, MN (US); Michael D. Delmore, Grant, MN (US); Michael K. Domroese, Woodbury, MN (US); Richard H. Ferber, Fridley, MN (US); Jay D. Jacobs, Sonoma, CA (US); Jamieson C. Keister, Lakeville, MN (US); Franklyn L. Frederickson, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 384 days.

(21) Appl. No.: 10/621,620

(22) Filed: Jul. 17, 2003

(65) Prior Publication Data

US 2005/0261631 A1    Nov. 24, 2005

Related U.S. Application Data

(60) Provisional application No. 60/397,372, filed on Jul. 19, 2002, provisional application No. 60/424,774, filed on Nov. 8, 2002.

(51) Int. Cl.
*A61M 5/00* (2006.01)
*A61M 37/00* (2006.01)
*A61K 9/00* (2006.01)
*A61K 9/70* (2006.01)

(52) U.S. Cl.
CPC .......... *A61M 37/0015* (2013.01); *A61K 9/0021* (2013.01); *A61K 9/7023* (2013.01); *A61M 2037/0023* (2013.01); *A61M 2037/0046* (2013.01); *A61M 2205/0244* (2013.01)
USPC ............................................. 604/173; 604/46

(58) Field of Classification Search
USPC ................................ 604/173, 4, 647; 606/186
See application file for complete search history.

(56) References Cited

U.S. PATENT DOCUMENTS

| | | | |
|---|---|---|---|
| 2,619,962 A | 12/1952 | Rosenthal |
| 3,034,507 A | 5/1962 | McConnell et al. |
| 3,072,122 A | 1/1963 | Rosenthal |
| 3,074,403 A | 1/1963 | Cooper et al. |
| 3,123,212 A | 3/1964 | Taylor et al. |
| 3,136,314 A | 6/1964 | Kravitz |

(Continued)

FOREIGN PATENT DOCUMENTS

| | | |
|---|---|---|
| EP | 0 407 063 A1 | 1/1991 |
| EP | 1 086 718 A1 | 3/2001 |

(Continued)

OTHER PUBLICATIONS

Msn Encarta definition of 'solid' http://encarta.msn.com/encnet/features/dictionary/DictionaryResults.aspx?refid=1861710192.*

(Continued)

*Primary Examiner* — Kevin C Sirmons
*Assistant Examiner* — Phillip Gray

(57) ABSTRACT

Microneedle devices with microneedles having a truncated tapered shape are disclosed. The microneedles of microneedle devices may also have a controlled aspect ratio. Microneedle delivery apparatus are disclosed that include drivers designed to deliver microneedles at velocities that may enhance perforation of the stratum corneum while limiting the sensation of pain experienced at the delivery site.

17 Claims, 8 Drawing Sheets

(56) References Cited

U.S. PATENT DOCUMENTS

| | | | |
|---|---|---|---|
| 3,221,740 A | 12/1965 | Rosenthal | |
| 3,246,647 A | 4/1966 | Taylor et al. | |
| 3,678,150 A | 7/1972 | Szumski et al. | |
| 3,905,371 A | 9/1975 | Stickl et al. | |
| 3,964,482 A * | 6/1976 | Gerstel et al. | 604/890.1 |
| 4,018,938 A | 4/1977 | Feder et al. | |
| 4,165,395 A | 8/1979 | Chang | |
| 4,237,906 A | 12/1980 | Havstad et al. | |
| 4,304,241 A | 12/1981 | Brennan | |
| 4,508,749 A | 4/1985 | Brannon et al. | |
| 4,523,807 A | 6/1985 | Suzuki | |
| 4,568,632 A | 2/1986 | Blum et al. | |
| 4,693,791 A | 9/1987 | Becker et al. | |
| 4,786,358 A | 11/1988 | Yamazaki et al. | |
| 4,822,975 A | 4/1989 | Torigoe | |
| 4,970,366 A | 11/1990 | Imatou et al. | |
| 5,045,439 A | 9/1991 | Maner et al. | |
| 5,055,163 A | 10/1991 | Bier et al. | |
| 5,073,237 A | 12/1991 | Bacher et al. | |
| 5,160,823 A | 11/1992 | Bennin et al. | |
| 5,250,023 A | 10/1993 | Lee et al. | |
| 5,262,128 A | 11/1993 | Leighton et al. | |
| 5,279,544 A | 1/1994 | Gross et al. | |
| 5,342,737 A | 8/1994 | Georger, Jr. et al. | |
| 5,389,954 A | 2/1995 | Inaba et al. | |
| 5,457,041 A | 10/1995 | Ginaven et al. | |
| 5,543,108 A | 8/1996 | Bacher et al. | |
| 5,611,806 A | 3/1997 | Jang | |
| 5,657,516 A | 8/1997 | Berg et al. | |
| 5,658,515 A | 8/1997 | Lee et al. | |
| 5,879,326 A | 3/1999 | Godshall et al. | |
| 5,983,136 A | 11/1999 | Kamen | |
| 6,050,988 A | 4/2000 | Zuck | |
| 6,090,790 A | 7/2000 | Eriksson | |
| 6,093,520 A | 7/2000 | Vladimirsky et al. | |
| 6,132,755 A | 10/2000 | Eicher et al. | |
| 6,183,434 B1 | 2/2001 | Eppstein | |
| 6,230,051 B1 | 5/2001 | Cormier et al. | |
| 6,256,533 B1 | 7/2001 | Yuzhakov et al. | |
| 6,312,612 B1 | 11/2001 | Sherman et al. | |
| 6,322,808 B1 | 11/2001 | Trautman et al. | |
| 6,331,266 B1 | 12/2001 | Powell et al. | |
| 6,334,856 B1 | 1/2002 | Allen et al. | |
| 6,379,324 B1 | 4/2002 | Gartstein et al. | |
| 6,451,240 B1 | 9/2002 | Sherman et al. | |
| 6,454,755 B1 | 9/2002 | Godshall | |
| 6,503,231 B1 | 1/2003 | Prausnitz et al. | |
| 6,532,386 B2 | 3/2003 | Sun et al. | |
| 6,533,949 B1 | 3/2003 | Yeshurun et al. | |
| 6,551,849 B1 | 4/2003 | Kenney | |
| 6,565,532 B1 | 5/2003 | Yuzhakov et al. | |
| 6,591,124 B2 | 7/2003 | Sherman et al. | |
| 6,595,947 B1 | 7/2003 | Mikszta et al. | |
| 6,603,998 B1 | 8/2003 | King et al. | |
| 6,605,332 B2 | 8/2003 | Calhoun et al. | |
| 6,652,478 B1 | 11/2003 | Gartstein et al. | |
| 6,663,820 B2 | 12/2003 | Arias et al. | |
| 6,686,299 B2 | 2/2004 | Montemagno et al. | |
| 6,713,291 B2 | 3/2004 | King et al. | |
| 6,743,211 B1 | 6/2004 | Prausnitz et al. | |
| 6,770,480 B1 | 8/2004 | Canham | |
| 6,797,276 B1 | 9/2004 | Glenn et al. | |
| 6,835,184 B1 | 12/2004 | Sage et al. | |
| 6,881,203 B2 | 4/2005 | Delmore et al. | |
| 6,899,838 B2 | 5/2005 | Lastovich | |
| 6,908,453 B2 | 6/2005 | Fleming et al. | |
| 6,931,277 B1 | 8/2005 | Yuzhakov et al. | |
| 8,236,368 B2 | 8/2012 | Jung et al. | |
| 2002/0016562 A1 | 2/2002 | Cormier et al. | |
| 2002/0020688 A1* | 2/2002 | Sherman et al. | 216/2 |
| 2002/0045859 A1* | 4/2002 | Gartstein et al. | 604/117 |
| 2002/0053756 A1 | 5/2002 | Powell et al. | |
| 2002/0082543 A1 | 6/2002 | Park et al. | |
| 2002/0095134 A1 | 7/2002 | Pettis et al. | |
| 2002/0123675 A1* | 9/2002 | Trautman et al. | 600/309 |
| 2002/0138049 A1 | 9/2002 | Allen et al. | |
| 2002/0169416 A1 | 11/2002 | Gonnelli et al. | |
| 2002/0177858 A1 | 11/2002 | Sherman et al. | |
| 2002/0198509 A1 | 12/2002 | Mikszta et al. | |
| 2003/0045837 A1 | 3/2003 | Delmore et al. | |
| 2003/0078549 A1 | 4/2003 | Stupar et al. | |
| 2003/0093040 A1 | 5/2003 | Mikszta et al. | |
| 2003/0095582 A1 | 5/2003 | Ackley | |
| 2003/0135161 A1 | 7/2003 | Fleming et al. | |
| 2003/0135167 A1* | 7/2003 | Gonnelli | 604/272 |
| 2003/0135201 A1 | 7/2003 | Gonnelli | |
| 2003/0148401 A1 | 8/2003 | Agrawal et al. | |
| 2003/0181936 A1 | 9/2003 | Trautman et al. | |
| 2003/0199810 A1 | 10/2003 | Trautman et al. | |
| 2004/0049150 A1 | 3/2004 | Dalton et al. | |
| 2004/0060902 A1 | 4/2004 | Evans et al. | |
| 2004/0077994 A1 | 4/2004 | Lastovich et al. | |
| 2004/0106904 A1 | 6/2004 | Gonnelli et al. | |
| 2004/0176732 A1 | 9/2004 | Frazier et al. | |
| 2005/0025778 A1 | 2/2005 | Cormier et al. | |
| 2005/0049549 A1 | 3/2005 | Wong et al. | |
| 2005/0049625 A1 | 3/2005 | Shaya et al. | |
| 2005/0065463 A1 | 3/2005 | Tobinaga et al. | |
| 2005/0106226 A1 | 5/2005 | Cormier et al. | |
| 2005/0118388 A1 | 6/2005 | Kingsford | |
| 2005/0137525 A1 | 6/2005 | Wang et al. | |
| 2005/0261631 A1 | 11/2005 | Clarke et al. | |

FOREIGN PATENT DOCUMENTS

| | | | |
|---|---|---|---|
| EP | 1 086 719 A1 | 3/2001 | |
| EP | 1 088 642 A1 | 4/2001 | |
| GB | 2 221 394 A | 2/1990 | |
| KR | 10-0781702 | 12/2007 | |
| WO | WO 94/25259 A1 | 11/1994 | |
| WO | WO 96/10630 * | 4/1996 | |
| WO | WO 96/10630 A1 | 4/1996 | |
| WO | WO 96/33839 A1 | 10/1996 | |
| WO | WO 97/03718 A1 | 2/1997 | |
| WO | WO 99/64580 A1 | 12/1999 | |
| WO | WO 00/05166 A1 | 2/2000 | |
| WO | WO 00/09184 A1 | 2/2000 | A61M 5/20 |
| WO | WO 00/74763 A2 | 12/2000 | |
| WO | WO 00/74763 A3 | 12/2000 | |
| WO | WO 00/74764 A1 | 12/2000 | |
| WO | WO 01/36037 A2 | 5/2001 | |
| WO | WO 01/91846 A2 | 12/2001 | |
| WO | WO 03/024507 A2 | 3/2003 | |
| WO | WO 03/026733 A2 | 4/2003 | |
| WO | WO 2005/051455 A2 | 6/2005 | |

OTHER PUBLICATIONS

Definition of 'solid': http://encarta.msn.com/encnet/features/dictionary/DictionaryResults.aspx?refid=1861710192.*

Merrian-Webster Online definition of 'truncated'. http://www.merriam-webster.com/dictionary/truncated.*

Daddona, P.; "Recent advances in peptide, protein and macromolecule drug delivery"; Current Opinion in Drug Discovery & Development 1999 2(2):168-171.

Kaushik, S et al.; "Lack of Pain Associated with Microfabricated Microneedles"; Anesth Analg; 2001, 92:502-504.

Henry S. et al.; "Microfabricated Microneedles: A Novel Approach to Transdermal Drug Delivery"; Journal of Pharmaceutical Sciences; vol. 87, No. 8, Aug. 1998 pp. 922-925.

(56) References Cited

OTHER PUBLICATIONS

McAllister, D. et al.; "Microfabricated Microneedles for Gene and Drug Delivery"; Annu. Rev. Biomed. Eng.; 2000; 02:289-313.

McAllister, D. et al.; "Solid and Hollow Microneedles for Transdermal Protein Delivery"; Proceed. In'tl. Symp. Control. Rel. Bioact. Materi., 26; Jul. 1999; Controlled Release Society, Inc.; pp. 192-193.

Griss, P. et al; Novel, Side Opened Out-of-Plane Microneedles for Microfluidic Transdermal Interfacing; IEEE; 2002; pp. 467-470.

Weber, L. et al.; "Micro molding—a powerful tool for the large scale production of precise microstructures"; SPIE vol. 2879; pp. 156-167.

Edwards, T. et al.; "Rapid Tooling Using SU-8 for Injection Molding Microfluidic Components"; Proceedings of SPIE, vol. 4177 (2000) pp. 82-89.

* cited by examiner

MICRONEEDLE DEVICES AND MICRONEEDLE DELIVERY APPARATUS

RELATED APPLICATIONS

This application claims the benefit of U.S. Provisional Application No. 60/397,372 filed 19 Jul. 2002 and titled MICRONEEDLE DEVICES AND MICRONEEDLE DELIVERY APPARATUS and U.S. Provisional Application No. 60/424,774 filed 8 Nov. 2002 and titled MICRONEEDLE DEVICES AND MICRONEEDLE DELIVERY APPARATUS, both of which are hereby incorporated by reference in their entireties.

BACKGROUND

Few molecules of demonstrated therapeutic value can be transported through the skin, even with the use of approved chemical enhancers. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Issues associated with microneedle devices include the ability to effectively pierce the stratum corneum. That ability can be compromised by the desire to limit the height of the microneedle structures to avoid stimulating the nerves located under the stratum corneum. As a result of the limited height of the structures, it may be difficult to reliably pierce the stratum corneum in enough locations to effectively deliver a therapeutic agent to a patient.

Another issue associated with known microneedle devices is the structural integrity of the microneedle structures themselves. Structures that are not robust may fracture or otherwise degrade when advanced through the stratum corneum. As a result, portions of the structures may be left imbedded in the skin. Although the structures are typically manufactured of biologically inert materials, it may be preferred that no portions of the structure remain in the skin after use.

SUMMARY OF THE INVENTION

The present invention provides microneedle devices, microneedle delivery devices, and methods of using microneedle devices. The microneedle devices, microneedle delivery apparatus, and methods of using the microneedles may all be used in concert, or they may be separately employed as desired.

The microneedle devices according to the present invention include microneedles protruding from a substrate, with the microneedles having a truncated tapered shape that preferably reduces tip fractures while still providing for effective perforation of the stratum corneum. The microneedles of microneedle devices according to the present invention may also have a controlled aspect ratio to enhance effective perforation of the stratum corneum.

The microneedle delivery apparatus according to the present invention include drivers designed to deliver microneedles at velocities that may enhance perforation of the stratum corneum while limiting the sensation of pain experienced at the delivery site. To accomplish those goals, the delivery apparatus may use components with limited mass to reduce the tendency of the apparatus to stimulate nerves during delivery of microneedle devices. The delivery apparatus may be designed to carry the microneedles towards the skin, or they may be designed with a mass that strikes the back surface of a microneedle device already placed in contact with the skin. In addition, the delivery apparatus may preferably include a pressure collar that is forced against the skin around the microneedle device to improve skin tautness as the microneedle device is moved through the skin.

In one aspect, the present invention provides a microneedle device including a substrate with a first major surface; and at least one microneedle projecting from the first major surface of the substrate, the at least one microneedle having a base proximate the first major surface of the substrate, wherein the at least one microneedle is tapered from the base to a flat tip distal from the base such that the at least one microneedle has a truncated tapered shape; wherein the flat tip has a surface area measured in a plane aligned with the base of 20 square micrometers or more and 250 square micrometers or less.

In another aspect, the present invention includes using a microneedle device of the present invention to contact skin on a patient and forcing the microneedle device against the skin.

In another aspect, the present invention provides a microneedle device including a substrate with a first major surface; and a plurality of microneedles projecting from the first major surface of the substrate, each microneedle of the plurality of microneedles having a base proximate the first major surface of the substrate, wherein each microneedle of the plurality of microneedles is formed of one or more polymers and is tapered from the base to a flat tip distal from the base such that each microneedle of the plurality of microneedles has a truncated tapered shape; wherein the flat tip has a surface area measured in a plane aligned with the base of 20 square micrometers or more and 100 square micrometers or less; wherein the base of each microneedle of the plurality of microneedles has a base area of 900 square micrometers or more; and wherein each microneedle of the plurality of microneedles has a height above the first major surface and a maximum base dimension, the height and the maximum base dimension ratio defining an aspect ratio, wherein the aspect ratio is 3:1 or more.

In another aspect, the present invention provides a microneedle device including a substrate with a first major surface; and at least one microneedle projecting from the first major surface of the substrate, the at least one microneedle having a base proximate the first major surface of the substrate, wherein the at least one microneedle is tapered from the base to a tip distal from the base such that the at least one microneedle has a truncated tapered shape having a height (h) above the first major surface as measured from the base to the tip; wherein the at least one microneedle has a cross-sectional area of 20 square micrometers or more and less than a base area of the at least one microneedle, where the cross-sectional area is measured in a plane aligned with the base, the plane being located at a distance of 0.98 h from the base.

In another aspect, the present invention provides a microneedle device including a substrate with a first major surface; and a plurality of microneedles projecting from the first major surface of the substrate, each microneedle of the plurality of microneedles having a base proximate the first major surface of the substrate, wherein each microneedle of the plurality of microneedles is formed of one or more polymers and is tapered from the base to a flat tip distal from the base such that each microneedle of the plurality of microneedles has a truncated tapered shape; wherein each microneedle of the plurality of microneedles has a cross-sectional area of 20 square micrometers or more and 25% or less of a base area of each microneedle of the plurality of microneedles, where the cross-sectional area is measured in a plane aligned with the base, the plane being located at a distance of 0.98 h from the base; wherein the base of each microneedle of the plurality of microneedles has a base area of 900 square micrometers or more; and wherein each microneedle of the plurality of microneedles has a maximum base dimension, the height and the maximum base dimension ratio defining an aspect ratio, wherein the aspect ratio is 3:1 or more.

In another aspect, the present invention provides a method of delivering a microneedle device, the method including: positioning a microneedle device proximate a delivery site on skin, the microneedle array having a plurality of microneedles protruding from a surface; and accelerating a piston having a face towards the microneedle device, wherein the piston has a minimum velocity of 4 meters per second or more and a maximum velocity of 10 meters per second or less when the face of the piston contacts the microneedle device.

In another aspect, the present invention provides a method of delivering a microneedle device, the method including: providing a microneedle delivery apparatus including a microneedle device with a plurality of microneedles protruding from a surface, the microneedle device being attached to a face of a piston, a driver operably connected to the piston; and accelerating the piston and the attached microneedle device towards the delivery site using the driver, wherein the piston has a minimum velocity of 4 meters per second or more and a maximum velocity of 10 meters per second or less when the microneedle device contacts the delivery site.

In another aspect, the present invention provides a microneedle delivery apparatus including a housing; a piston located within the housing; a driver operably connected to the piston, wherein the driver has stored energy, wherein release of the stored energy results in acceleration of the piston toward a delivery site; and means for marking skin at the delivery site towards which the piston accelerates.

In another aspect, the present invention provides a microneedle delivery apparatus including a housing; a piston located within the housing; a driver operably connected to the piston, wherein the driver has stored energy, wherein release of the stored energy results in acceleration of the piston toward a delivery site to a minimum velocity of 4 meters per second or more and a maximum velocity of 10 meters per second or less when the face of the piston reaches the delivery site.

In another aspect, the present invention provides a microneedle delivery apparatus including a housing; a piston located within the housing; a driver operably connected to the piston, wherein the driver has stored energy, wherein release of the stored energy results in acceleration of the piston toward a delivery site; and a pressure collar on an exterior of the housing.

These and other features and advantages of the invention may be described below in connection with various illustrative embodiments of the invention.

DETAILED DESCRIPTION OF ILLUSTRATIVE EMBODIMENTS OF THE INVENTION

The present invention provides microneedle devices that may be useful for a variety of purposes. For example, the microneedle devices may be used to pierce the stratum corneum at a delivery site on a patient's skin. For example, the microneedle devices may be used to deliver drugs (including any pharmacological agent or agents) through the skin in a variation on transdermal delivery. Where the microneedle devices are to be used for piercing the stratum corneum in preparation for transdermal drug delivery, the height of the microneedles is preferably sufficient to pass through the stratum corneum. It is also, however, preferable that the height of the microneedles is not sufficiently large to cause significant pain when inserted at a delivery site.

In some embodiments, the microneedle devices may be left in place during drug administration with the drug moving through or around the microneedles to pass through the pierced sites in the stratum corneum. Alternatively, the microneedle devices may be removed from the skin after piercing the stratum corneum and a drug may be applied to the treated site (e.g., in the form of a transdermal drug delivery patch, a topical lotion, etc.), such that the drug can pass through the pierced stratum corneum.

As used in connection with the present invention, the term "microneedle" (and variations thereof) refers to structures having a height above the surface from which they protrude of about 500 micrometers or less. In some instances, microneedles of the present invention may have a height of about 250 micrometers or less.

Although the illustrative microneedle devices described herein may include multiple microneedles, it will be understood that microneedle devices of the present invention may include only one microneedle on each substrate. Further, although the microneedle devices are all depicted with only one substrate, each device could include multiple substrates, with each substrate including one or more microneedles protruding therefrom.

Figure 1:
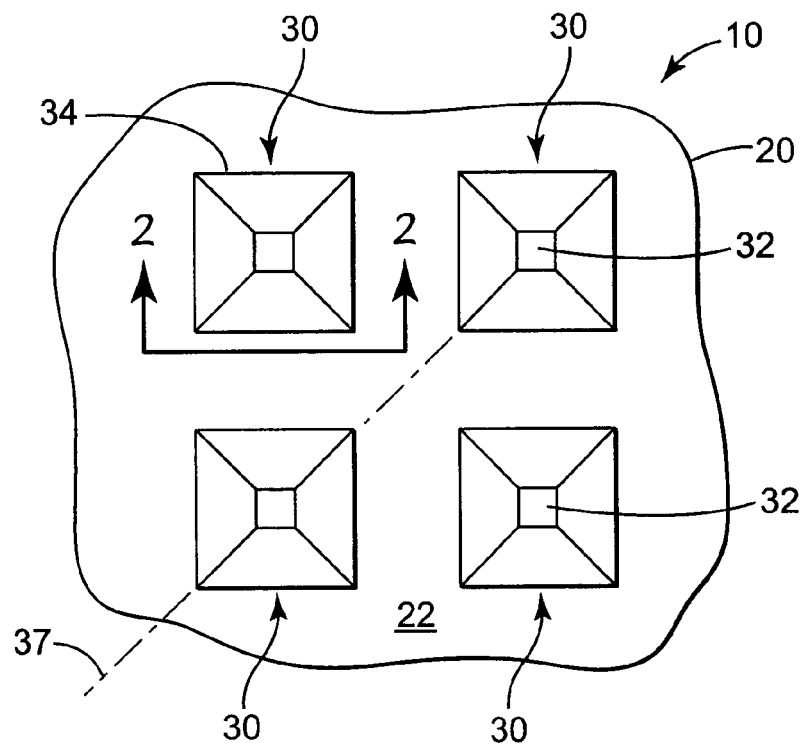
FIG. 1 is an enlarged plan view of a portion of one microneedle device according to the present invention.
Figure 2:
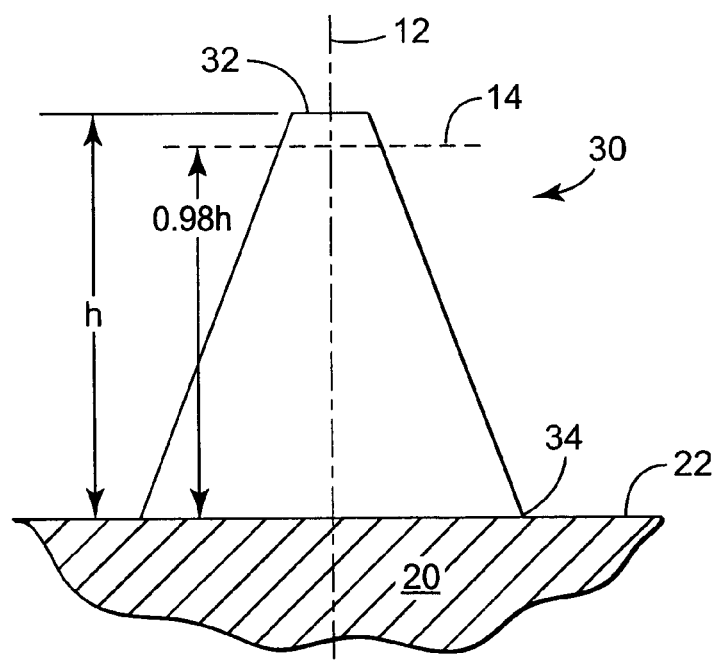
FIG. 2 is a cross-sectional view of one microneedle of the microneedle device of FIG. 1, taken along line 2-2 in FIG. 1.

Referring now to FIGS. 1 and 2, a portion of one microneedle device 10 is illustrated with microneedles 30 protruding from a surface 22 of a microneedle substrate 20. The microneedles 30 may be arranged in any desired pattern or distributed over the surface 22 randomly.

The microneedles 30 each include a base 34 proximate the substrate surface 22 and a top surface 32 distal from the base 34. The general shape of the microneedles 30 is preferably tapered. For example, the microneedles 30 have a larger base 34 at the substrate surface 22 and extend away from the substrate surface 22, tapering towards the top surface 32.

Although the microneedles 30 of FIGS. 1 & 2 are quadrangular pyramids with four sided bases, it should be understood that the microneedles may take any suitable shape, e.g., triangular pyramids, etc. Furthermore, the pyramid-shaped microneedles may or may not be regular pyramids. It should also be noted that the microneedles 30 are not true pyramids. Rather, they are truncated pyramids including a top surface 32 that may preferably be flat. The top surface 32 may be located in a plane that is parallel to the base 34 of the microneedle 30 (in which case the microneedle 30 can be identified as a frustum of a pyramid). Alternatively, the top surface 32 may be located in a plane that is not parallel to the base 34.

By providing the microneedles 30 with blunt or flat top surfaces 32 in contrast to full pyramids (that include a tip at which all sides of the pyramid meet), the structural integrity of the microneedles 30 may be improved relative to the structural integrity of microneedles in the form of full pyramids. As noted above, microneedles in the form of full pyramids may suffer from fracture when stressed, e.g., during insertion of the microneedles through the stratum corneum. The fractured microneedles may leave debris in, e.g., the stratum corneum.

The issue of structural integrity may be most prominent when the microneedles are manufactured from polymeric materials as opposed to metallic or silicon microneedle structures. If polymeric materials are used to form the microneedles, it may be preferred the polymeric materials have one or more of the following properties: moldable (by, e.g., injection molding, compression molding, etc.), have a high modulus of elasticity, and high elongation at break.

Among polymeric materials, it may be preferred that the microneedles be manufactured of thermoplastic polymeric materials. Suitable polymeric materials for the microneedles of the present invention may include, but are not limited to: acrylonitrile-butadiene-styrenes, polyphenyl sulfides, polycarbonates, polypropylenes, acetals, acrylics, polyetherimides, polybutylene terephthalates, polyethylene terephthalates, etc. Polymeric microneedles may be manufactured of a single polymer or a mixture/blend of two or more polymers.

Although the microneedles 30 of FIGS. 1 & 2 are depicted with flat top surfaces 32, it should be understood that the top surfaces 32 need not be perfectly planar. Rather, the top surfaces 32 may exhibit some variations from a purely planar surface and still fall within the scope of the term "flat" as used herein. For example, the top surfaces 32 may be rounded, domed, or otherwise deviate from a planar surface.

In another manner of characterizing the truncated, tapered microneedles of microneedle devices according to the present invention, the cross-sectional surface area of the microneedles at a selected setback distance from the base may be described. The microneedle 30 of FIG. 2 is depicted as having a height h as measured between the base 34 and the top. In the case of microneedle 30, the top is the top surface 32 and the height h of the microneedle 30 is measured along its central axis 12. In this manner of characterizing the truncated tapered microneedles of the present invention, the cross-sectional area of the microneedle 30 may be measured in a plane 14 (seen on edge in FIG. 2) that is aligned with the base 34 and is located at a setback distance of 0.98 h, i.e., 0.02 h from the top of the microneedle 30. By describing that the plane 14 is aligned with the base 34, it is meant that the plane is generally parallel to the base, although slight variations from a true parallel relationship are permitted.

At the setback distance at which plane 14 is located along the central axis 12, the microneedle 30 may, for example, have a preferred cross-sectional area of 20 square micrometers or more. At the other end of the range, the microneedle 30 has a cross-sectional area within plane 14 at the setback distance that is less than the base area of the microneedle as discussed below. In some instances, it may be preferred that the cross-sectional area at the setback distance be 25% or less of the base area of the microneedle. In other instances, it may be preferred that the microneedle have a cross-sectional surface area of 100 square micrometers or less. In still other instances, it may be preferred that the cross-sectional surface area at the setback distance be 50 square micrometers or less.

In connection with the cross-sectional area of the microneedle 30 at the setback distance as described above, it may be possible to also characterize the area occupied by the base 34 of the microneedle 30 on the first major surface 22 of the substrate 20. For example, the base area (i.e., the area occupied by the base 34) may preferably be 900 square micrometers or more, and in some instances 1200 square micrometers or more. When coupled with the cross-sectional area at the setback distance or the surface area of the flat tips as described above, the base area may be useful as another manner of characterizing the truncated tapered shape of the microneedles of the present invention.

Figure 3:
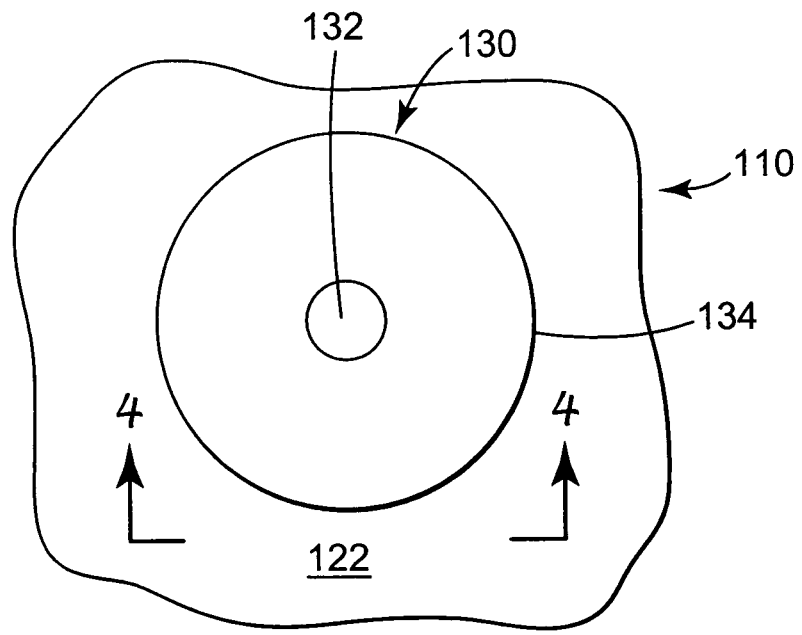
FIG. 3 is a plan view of one alternative microneedle on a microneedle device the present invention.
Figure 4:
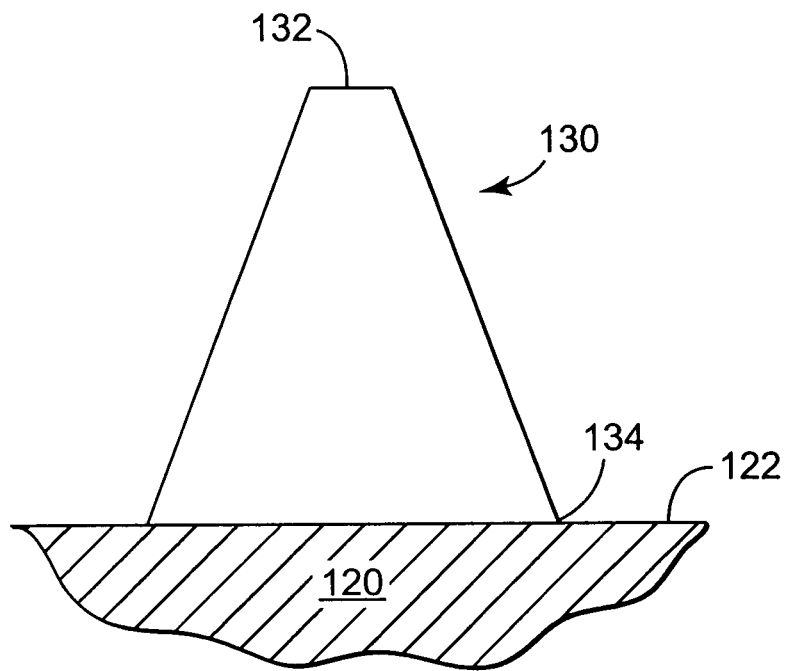
FIG. 4 is a cross-sectional view taken along line 4-4 in FIG. 3.

As noted above, the microneedles of microneedle devices according to the present invention are tapered from a wider base towards a narrower top surface. FIGS. 3 & 4 depict a conical microneedle 130 on a microneedle device 110 to illustrate that the tapered microneedles need not be in the form of pyramids.

The conical microneedle 130 includes a circular base 134, although other shapes for the base are also possible, e.g., elliptical, oval, crescent-like, etc. Although the microneedle 130 is depicted as a regular cone, it should be understood that conical microneedles of the present invention need not be in the form of regular cones.

Like the truncated pyramids described above, the microneedle 130 is also a truncated cone that terminates in a flat top surface 132 opposite the base 134 that is proximate the surface 122 of the substrate 120. The top surface 132 may be located in a plane that is parallel to the base 134 of the microneedle 130 (in which case the microneedle 130 can be identified as a frustum of a cone). Alternatively, the top surface 132 may be located in a plane that is not parallel to the base 134.

By providing conical microneedle 130 with a blunt or flat top 132 in contrast to a full cone (that includes a tip at which the cone terminates distal from the base), the structural integrity of the conical microneedle 130 may be improved relative to the structural integrity of a microneedle in the form of a full cone. As noted above, microneedles in the form of full cones may suffer from fracture when stressed, e.g., during insertion of the microneedles through the stratum corneum. The fractured microneedles may leave debris in, e.g., the stratum corneum.

Although the microneedle 130 of FIGS. 3 & 4 is depicted with a flat top surface 132, it should be understood that the top surface 132 need not be perfectly planar. Rather, the top surface 132 may exhibit some variations from a purely planar surface and still fall within the scope of the term "flat" as used herein.

Microneedles in microneedle devices of the present invention may be characterized in a number of different manners. One example is by surface area of the flat top associated with the truncated tapered shape of the microneedles. The surface area of the flat tops, e.g., top surface 32 in FIGS. 1 & 2 or top surface 132 in FIGS. 3 & 4, may, for example, have a preferred surface area of 100 square micrometers or less. In other instances, it may be preferred that the top have a surface area of 50 square micrometers or less. In still other instances, it may be preferred that the top have a surface area of 30 square micrometers or less.

By providing truncated tapered microneedles, microneedle devices of the present invention may provide for effective penetration of, e.g., the stratum corneum, without stimulating the underlying nerve tissue that would result in the sensation of pain. As used herein, "effective penetration" means that the pathways opened through the stratum corneum by microneedles with larger tops may provide for enhanced transfer of materials through the stratum corneum. In addition, the tapered shape of the microneedles may enhance penetration of the stratum corneum as compared to microneedles with more column-like shapes that are not tapered.

Another manner in which the microneedles of microneedle devices of the present invention may be characterized is based on the aspect ratio of the microneedles. As used herein, the term "aspect ratio" is the ratio of the height of the microneedle (above the surface surrounding the base of the microneedle) to the maximum base dimension, that is, the longest straight-line dimension that the base occupies (on the surface occupied by the base of the microneedle). For example, in the case of the quadrangular pyramid-shaped microneedles of FIGS. 1 & 2, the maximum base dimension would be measured between opposing corners of the microneedles (see, e.g., line 37 in FIG. 1). In the case of a conical microneedle with a circular base 134 as seen in FIGS. 3 & 4, the maximum base dimension would be the diameter of the base 134. In connection with the present invention, it may be preferred that the microneedles have an aspect ratio of 2:1 or higher, and in some instances 3:1 or higher.

Although not depicted, the microneedle devices may include other features such as channels which are described in U.S. patent application Ser. No. 09/947,195, filed on Sep. 5, 2001 and entitled MICRONEEDLE ARRAYS AND METHODS OF MANUFACTURING THE SAME. Furthermore, the microneedle devices may include covers pierced by the microneedles as described in U.S. patent application Ser. No. 10/051,745, filed on Jan. 15, 2002 and entitled MICRONEEDLE DEVICES AND METHODS OF MANUFACTURE.

Furthermore, although the microneedles and the substrate surfaces of the depicted embodiments are shown with relatively smooth surfaces, the various features of the microneedle devices may have surfaces that are not smooth, e.g., the surfaces may be roughened, structured, etc. to enhance fluid flow over the surface.

The microneedles may preferably be manufactured integrally with the substrate. In other words, the various features may preferably formed as a one piece, completely integral unit. Alternatively, the microneedles may be provided separately from the substrate.

The microneedle substrates may be manufactured from a variety of materials. Material selection may be based on a variety of factors including the ability of the material to accurately reproduce the desired pattern; the strength and toughness of the material when formed into the microneedles; the compatibility of the material with, for example, human or animal skin; the compatibility of the materials with any fluids that will be expected to contact the microneedle devices, etc.

Some suitable processes for forming microneedles of the present invention may be described in connection with U.S. patent application Ser. No. 09/947,195, filed on Sep. 5, 2001, and entitled MICRONEEDLE ARRAYS AND METHODS OF MANUFACTURING THE SAME.

In addition to including microneedles with a morphology that enhances structural integrity (that is, a truncated tapered shape), it may be preferred to provide the microneedle arrays in combination with microneedle delivery apparatus that are capable of delivering the microneedle arrays to a delivery site on skin in a manner that results in effective piercing of the stratum corneum by the microneedles on the microneedle device.

Delivery of a microneedle device in accordance with the methods of the present invention may involve acceleration of the microneedle device itself to a desired velocity. Alternatively, the methods may involve acceleration of a piston to a desired velocity that impacts the microneedle device (if it is already located on the skin).

In addition to acceleration of the microneedle devices themselves or pistons used to impact the microneedle devices to desired velocities to achieve perforation of the stratum corneum, it may also be useful to optionally provide a pressure collar in contact with the skin surrounding the delivery site to increase the tautness of the skin within the delivery site.

Following perforation of the stratum corneum by a microneedle device in accordance with the present invention, the microneedle device and the microneedle delivery apparatus used to force the microneedles through the stratum corneum may preferably be removed from the delivery site to allow for the application of, e.g., a transdermal drug delivery device, to the delivery site. Alternatively, the material desired to be passed through the stratum corneum may be applied to the delivery site in any other suitable manner, e.g., painting, etc.

Figure 5:
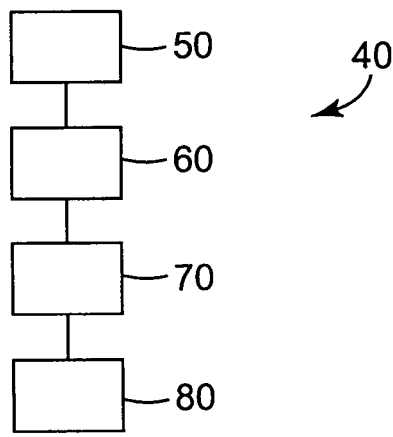
FIG. 5 is a block diagram of one microneedle delivery apparatus according to the present invention.

FIG. 5 is a block diagram of one illustrative microneedle delivery apparatus of the present invention. The apparatus 40 includes a driver 50, piston 60, optional pressure collar 70, and an optional microneedle device 80.

The driver 50 may be provided by any mechanism capable of providing acceleration sufficient to reach the desired velocities as discussed herein. For example, the driver 50 may be in the form of a mechanical spring (e.g., a coil spring, leaf spring, etc.), compressed resilient member (e.g., rubber, etc.), compressed fluids (e.g., air, liquids, etc.), piezoelectric structure, electromagnetic structure, hammer device, etc. Regardless of the precise form of the driver 50, it should be capable of storing sufficient energy to accelerate the mass of the piston 60 and (optionally) any attached microneedle device 80.

In the apparatus 40, the pressure collar 70 may be optionally employed to improve skin tautness within a delivery site. Examples of some pressure collars are described in more detail below with respect to two illustrative embodiments of microneedle delivery apparatus.

The microneedle device 80 is optionally a part of the apparatus 40 because, in some instances, the microneedle device 80 may be separately placed on the skin within the delivery site. In a system or method in which the microneedle device 80 is placed on the skin before impact, the piston 60 is preferably accelerated to the desired velocity before it impacts the microneedle device 80. In the depicted apparatus, however, the microneedle device 80 is attached to the piston 60 before the piston 60 is accelerated. As a result, both the piston 60 and the microneedle device 80 are accelerated together.

As discussed above, the methods of microneedle device delivery involve reaching a desired velocity that is effective to force the microneedles through the stratum corneum layer of the skin. The desired velocity is, however, preferably controlled to limit or prevent stimulation of the underlying nerve tissue that would result in the sensation of pain. In connection with the present invention, the maximum velocity achieved by the piston may preferably be 20 meters per second (m/s) or less, potentially 15 m/s or less, or possibly 10 m/s or less. In some instances, it may be more preferred that the maximum velocity be 8 m/s or less. At the lower end of the range of desired velocities, it may be preferred that the desired minimum velocity achieved by the piston be 2 m/s or more, possibly 4 m/s or more, possibly more preferably 6 m/s or more.

Figure 6:
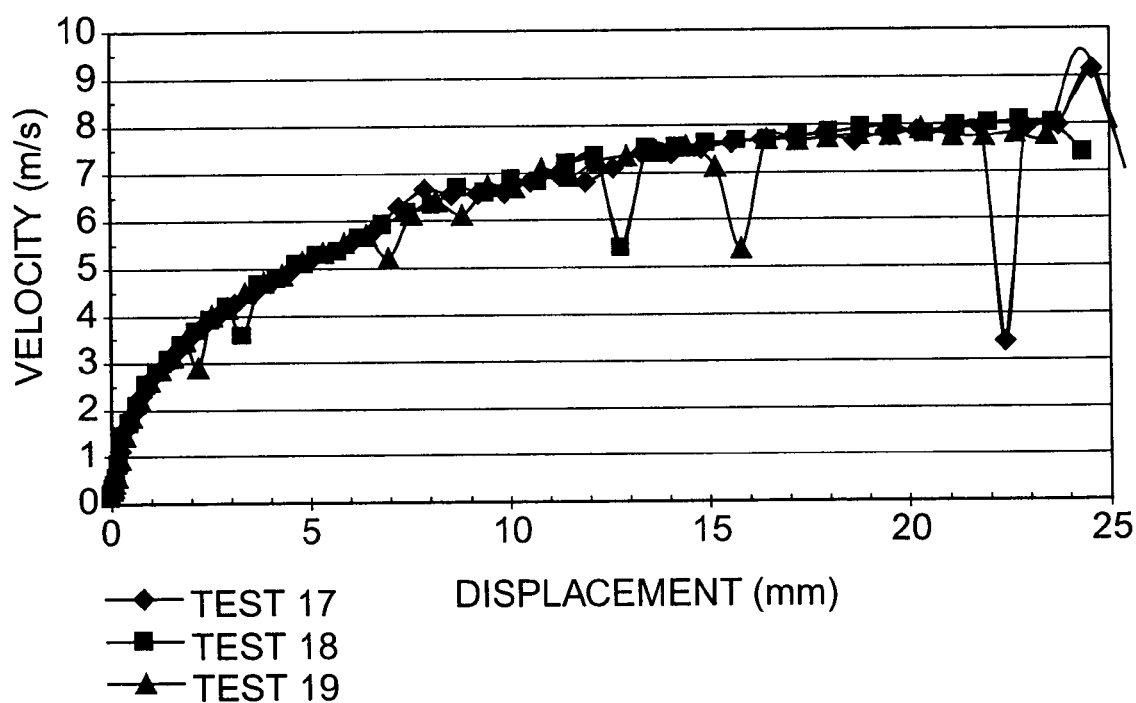
FIG. 6 is a graph of velocity (vertical axis) versus displacement (horizontal axis) for one microneedle delivery apparatus according to the present invention.
Figure 7:
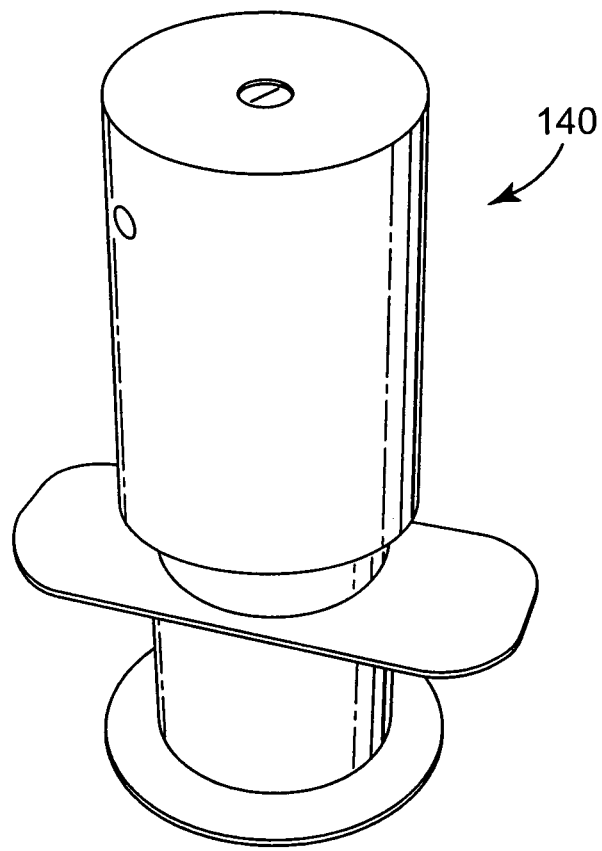
FIG. 7 is a perspective view of one microneedle delivery apparatus according to the present invention.

Referring to FIG. 6, another potentially advantageous characteristic of the methods of the present invention may be that the desired velocity be maintained over a sufficient displacement distance to result in effective perforation of the stratum corneum. As seen in FIG. 6, the maximum velocity of about 8 m/s is maintained over a significant displacement distance.

Another characteristic that can be described with respect to FIG. 6 is that the piston (and any attached microneedle device) be located a sufficient distance away from the delivery site to allow the piston to reach the desired maximum velocity before impact occurs. That impact may be of the piston with a microneedle device already in contact with the skin or of a microneedle device with the skin (where the microneedle device is attached to the piston). For example, with respect to FIG. 6, that distance may be about 7 millimeters or more.

Another potential characteristic of microneedle delivery apparatus according to the present invention that may discussed with respect to FIG. 6 is the distance over which the piston travels at or above the minimum velocity required for effective piercing of the stratum corneum by the microneedle device. It may be preferred that the distance over which the piston travels at or above the minimum velocity be sufficient to accommodate variations in the location of the skin surface at the delivery site. The location of the skin surface relative to the microneedle delivery apparatus may be somewhat variable due to a variety of factors. For example, the location of the skin surface may vary based on the magnitude of the force used to press the apparatus against the skin at the delivery site, the tautness of the skin at the delivery site (e.g., skin on the hand will typically be more taut than skin on, e.g., the abdomen). As a result, the skin may be located in a different position with respect to the apparatus when used on, e.g., the hand or the abdomen.

Because of the variability in the location of skin, it may be preferred that the apparatus be designed such that the piston travels at a velocity at or above the desired minimum velocities over a distance that is sufficient to accommodate the variations in skin location relative to the microneedle delivery apparatus. For example, it might be preferred that the piston in a microneedle delivery apparatus moves at or above the minimum velocity over a distance of one centimeter or more. In some embodiments, it may be sufficient that the piston move at or above the minimum velocity over a distance of 5 millimeters or more.

The force required to reach the desired velocities may vary based on the mass of the piston 60 (and any attached optional microneedle device 80). That mass may also be controlled or selected to reduce the likelihood that nerve tissue underneath the delivery site is stimulated sufficiently to result in the sensation of pain. For example, it may be preferred that the mass of the piston be 4 grams or less, possibly more preferably 2 grams or less.

These masses may also be affected by the size of the microneedle devices being used to perforate the stratum corneum. For example, the masses described above may be potentially advantageously used with microneedle devices occupying a surface area on the skin of 4 square centimeters or less, possibly more preferably about 2 square centimeters or less. Larger microneedle devices may be used with a higher velocity delivery apparatus because the force is effectively distributed over a larger surface area at the delivery site.

A variety of apparatus may be used to deliver microneedle devices in accordance with the present invention. One illustrative microneedle delivery apparatus 140 is depicted in FIGS. 7-10. The apparatus 140 is in the form of a plunger-type device using a coil compression spring 150 as a driver to accelerate a piston 160 with a face 162 towards the opening 142 in lower housing 144. That opening 142 is typically located over a delivery site on skin.

Figure 8:
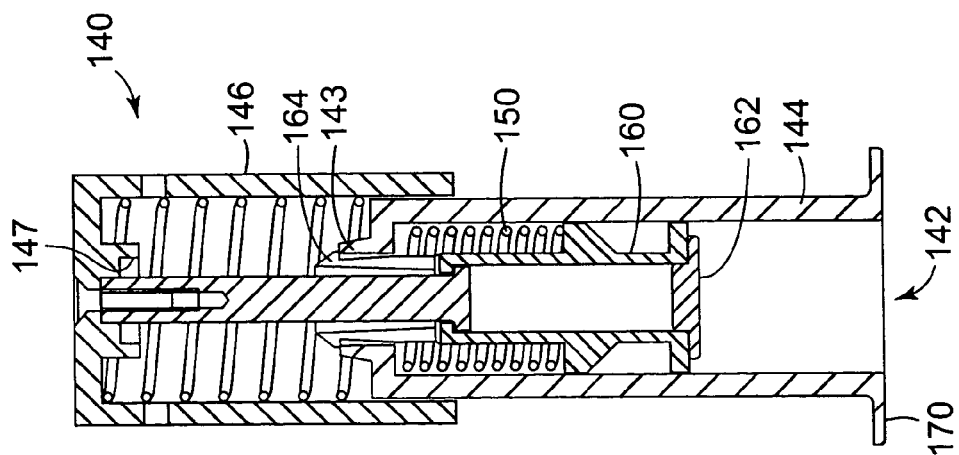
FIG. 8 is a cross-sectional view of the microneedle delivery apparatus of FIG. 7 in the cocked position.
Figure 11:
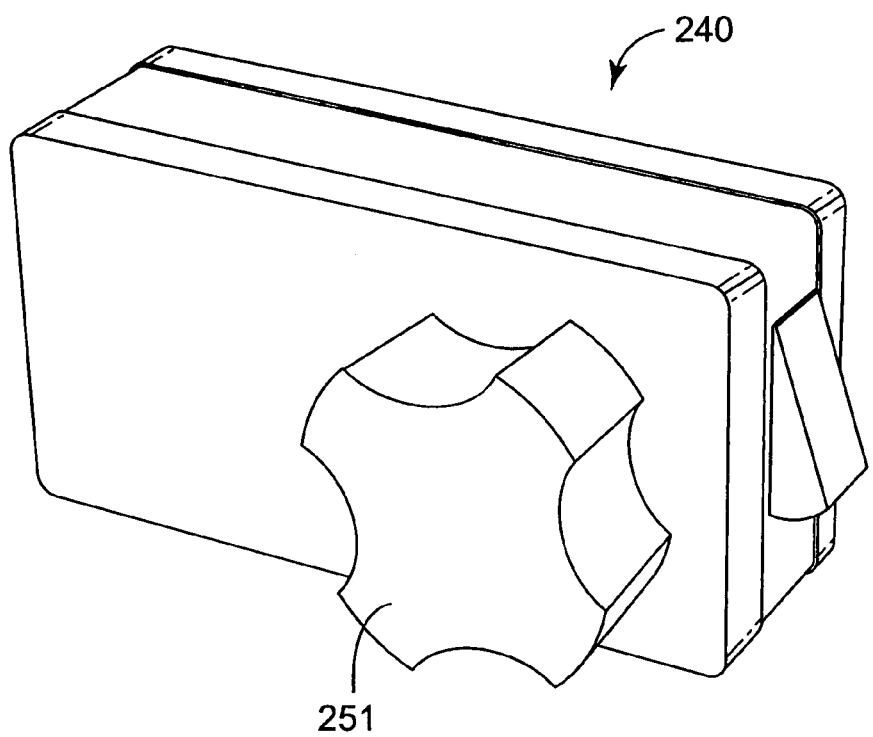
FIG. 11 is a perspective view of another microneedle delivery apparatus according to the present invention.
Figure 12:
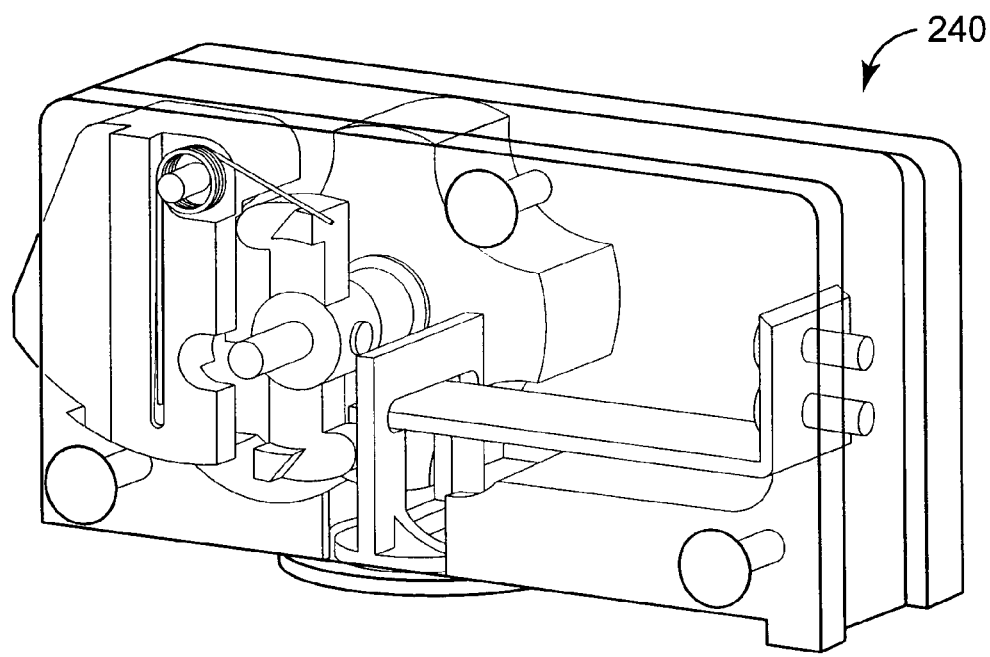
FIG. 12 is a transparent image of the microneedle delivery apparatus of FIG. 11 depicting components within the outer housing of the apparatus.

Referring to FIG. 8, the apparatus 140 includes an upper housing 146 that is pulled upward, that is, away from the opening 142 to draw the plunger 160 away from the opening 142 and compress the spring 150. When in its uppermost position as seen in FIG. 8, locking levers 164 on piston 160 engage shoulders 143 on lower housing 144 to retain the plunger 160 in the position seen in FIG. 8.

Figure 10:
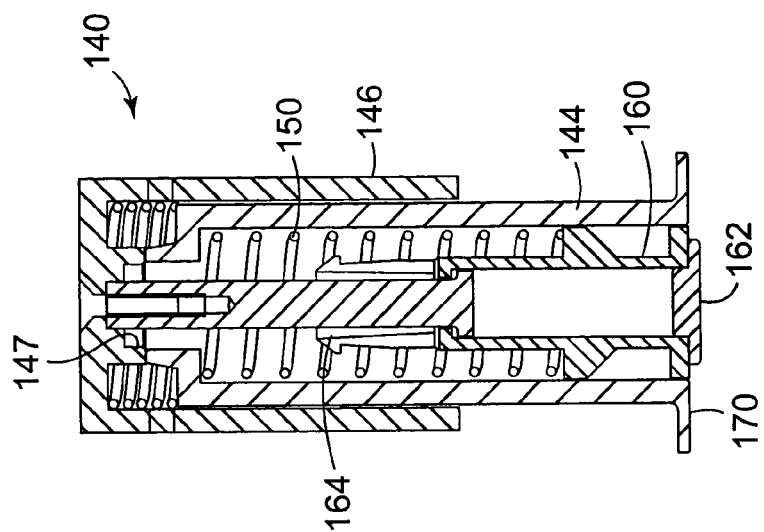
FIG. 10 is a cross-sectional view of the microneedle delivery apparatus of FIG. 8 in the fired position.
Figure 9:
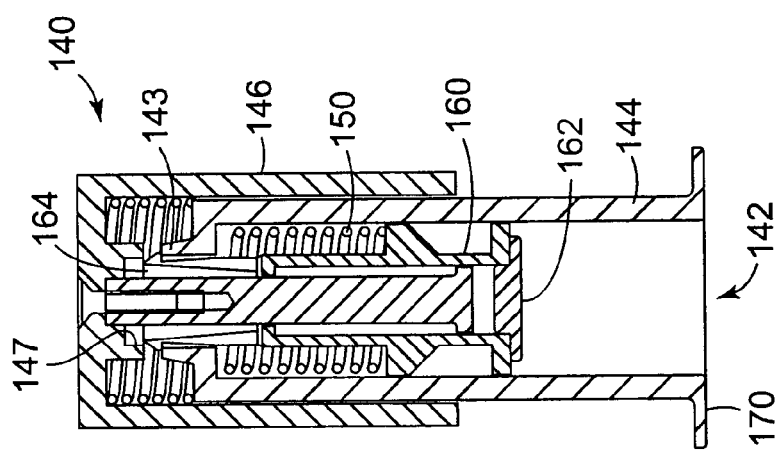
FIG. 9 is a cross-sectional view of the microneedle delivery apparatus of FIG. 8 in the release position.

Turning to FIG. 9, as the upper housing 146 is moved downward towards the opening 142, release portions 147 on the upper housing 146 cause the locking levers 164 to release from shoulders 143. As the locking levers 164 release, the spring 150 forces the piston 160 towards the opening 142 as seen in FIG. 10.

Another feature depicted in connection with microneedle delivery apparatus 140 is a pressure collar 170 that surrounds the opening 142. The pressure collar 170 is preferably placed in contact with the skin surrounding a delivery site during use of the apparatus 140. By forcing the pressure collar against the skin, tautness of the skin within the delivery site may be increased which may have a beneficial result in perforation of the stratum corneum.

Although the depicted pressure collar 170 is circular and would provide for continuous contact about the periphery of a delivery site, it will be understood that pressure collars used in connection with the microneedle delivery apparatus of the present invention could be provided in a variety of shapes and configurations. For example, the pressure collars may be discontinuous; that is, they may include gaps about the periphery of a delivery site.

Another feature that can be seen in connection with FIGS. 8 & 9 is that the apparatus 140 preferably is designed to locate the piston face 162 a sufficient distance from the opening 142 such that the desired maximum velocity of the piston can be reached by the time the piston reaches the opening 142.

Figure 13:
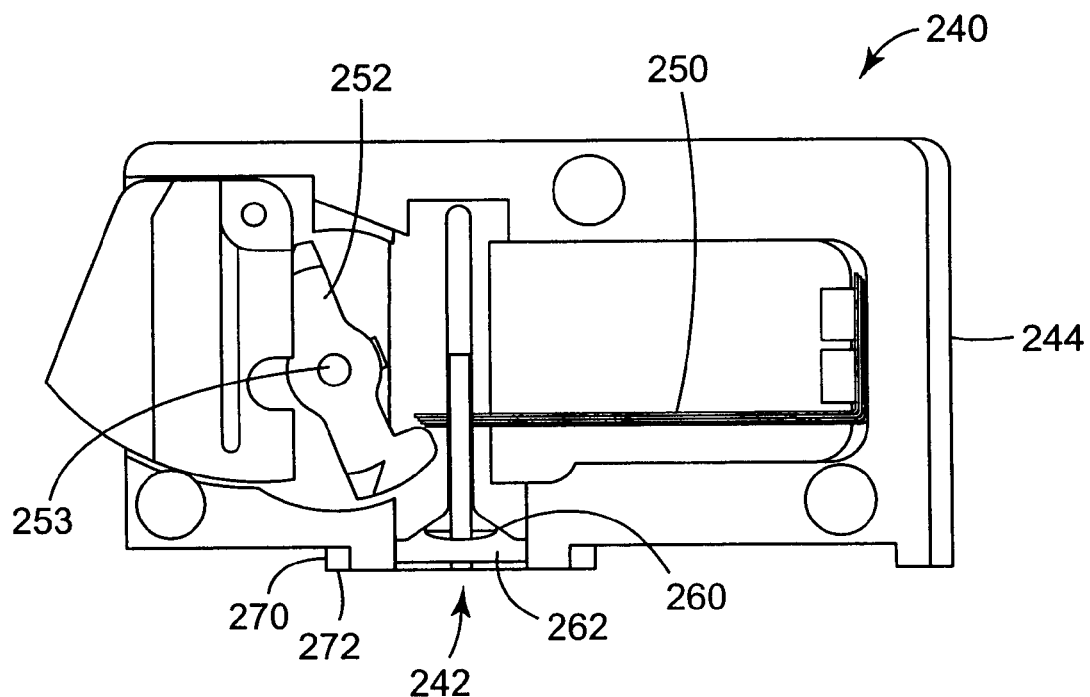
FIG. 13 is a view of the microneedle delivery apparatus of FIG. 11 with the housing removed to expose the interior of the apparatus during loading of the springs.
Figure 14:
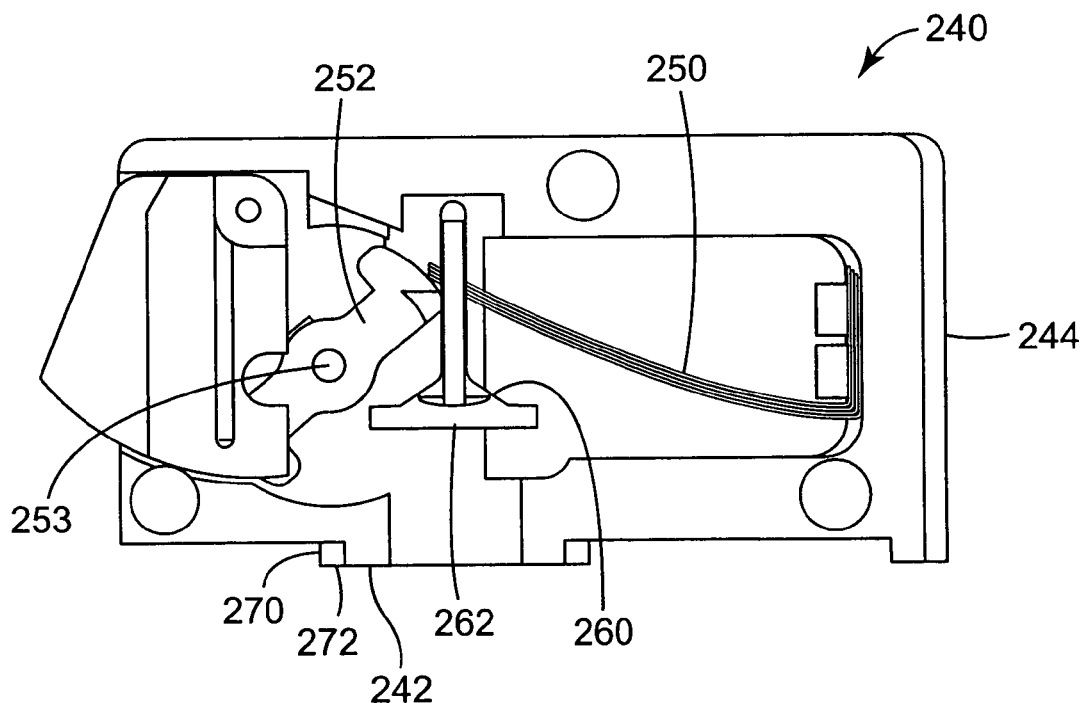
FIG. 14 is a view of the microneedle delivery apparatus of FIG. 13 with the springs fully loaded.

Another illustrative microneedle delivery apparatus 240 is depicted in connection with FIGS. 11-15. The apparatus 240 uses leaf springs 250 to provide the acceleration of a piston 260. Leaf springs 250 are deflected by a rotor 252, with the beginning stage of deflection being seen in FIG. 13 where rotor 252 contacts the leaf springs 250. As rotor 252 is rotated about an axis extending through pin 253, the leaf springs 250 are deflected until the position seen in FIG. 14, at which point the rotor 252 is preferably locked in position. Pin 253 is connected to knob 251 and as knob 251 is rotated, pin 253 and rotor 252 rotate as depicted in FIGS. 13 & 14.

Figure 15:
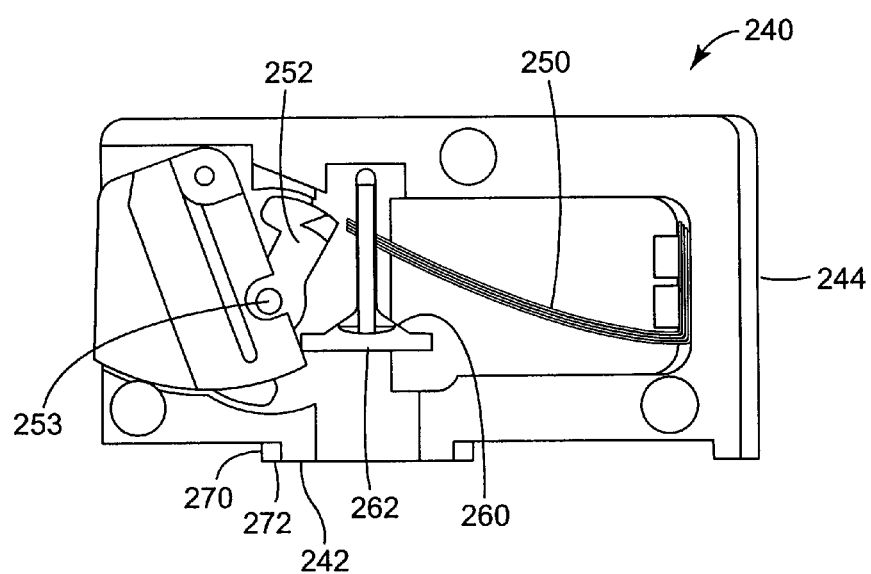
FIG. 15 is a view of the microneedle delivery apparatus of FIG. 13 in the release position.

Actuator button 254 is then pushed inward as seen in FIG. 15 to release the leaf springs 250 from rotor 252, thus allowing the leaf springs 250 to drive the plunger 260 and its face 262 towards opening 242 in the housing 244.

The housing 244 also includes a pressure collar 270 that may be used to improve skin tautness at a delivery site as described above. As depicted in FIGS. 13-15, the pressure collar 270 may preferably be generally planar in nature.

The illustrative microneedle delivery apparatus described herein may be designed for a single-use, with the apparatus being disposed after initial use. Alternatively, the apparatus may be designed for repeated uses with different microneedle devices.

Another feature that may be provided in connection with microneedle delivery apparatus is the ability to mark the delivery site on the patient with a marking composition such as, e.g., ink. Marking may be helpful to indicate where the stratum corneum has been pierced by the microneedles of the microneedle device. In the microneedle delivery apparatus 240, the marking may be accomplished by, e.g., providing a marking composition on the face 272 of the pressure collar 270. Other marking techniques may be used in place of a marking composition on the face 272 of pressure collar 270. Other means for delivering a marking composition may also be used, e.g., one or more spray devices may be used to deliver a marking composition in a manner that indicates the location of the delivery site. Another potential means for marking may be a marking device (e.g., pen, ink stamp, etc.) that is not an integral part of the microneedle delivery apparatus may also be used to mark the location of the delivery site before the microneedle delivery apparatus is used to deliver a microneedle device. It should be understood that delivery of microneedle devices and the microneedle delivery apparatus described herein may not necessarily be limited to use with the microneedle devices including microneedles with truncated tapered shapes as described above in connection with FIGS. 1-4.

Microneedle devices of the present invention may be used for a variety of purposes. For example, the microneedles may be used to deliver drugs or other pharmacological agents through the skin in a variation on transdermal delivery. When used for transdermal drug delivery, the microneedle devices may be left in place to facilitate drug delivery or they may be removed prior to application of a drug to the skin.

In one aspect, the microneedle devices are applied to the skin and subsequently removed as a pretreatment step. A drug is then applied to the skin area that has been treated with the microneedle device. The drug may be applied in any convenient manner, and the type of vehicle and duration of application will depend on the particular therapeutic outcome desired. In a one-time application, the drug may be in the form of a solution that is swabbed on the treated skin surface or as a cream that is rubbed into the treated skin surface. Alternatively, the drug may be applied to the surface in a form such that it remains in contact with the skin for an extended time. Extended contact may be effected by applying the drug in the form of a transdermal patch or a reservoir chamber that is affixed to the skin.

Microneedle devices of the present invention may have utility for a number of drugs and therapeutic indications. In one aspect, drugs that are of a large molecular weight may be delivered transdermally. It is commonly accepted that increasing molecular weight typically causes a decrease in unassisted transdermal delivery. Microneedle devices of the present invention have utility for the delivery of large molecules that are ordinarily difficult or impossible to deliver by passive transdermal delivery. Examples of such large molecules include proteins, peptides, polysaccharides, such as heparin, and antibiotics, such as ceftriaxone.

In another aspect, microneedle devices of the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle devices of the present invention may have utility for enhancing or altering transdermal delivery of molecules that may be delivered using passive transdermal delivery, such as nitroglycerin or estradiol. In such cases, the microneedle devices may be used to cause a more rapid onset of delivery or to cause an increased flux when compared to unassisted passive delivery.

In another aspect, microneedle devices of the present invention may have utility for enhancing delivery of molecules to the skin, such as in dermatological treatments or in enhancing immune response of vaccine adjuvants.

EXAMPLES

The following non-limiting examples are provided to assist with an understanding of the invention.

Example 1

Microneedle arrays were prepared using the general methods described in U.S. patent application Ser. No. 09/947,195, filed on Sep. 5, 2001 and entitled MICRONEEDLE ARRAYS AND METHODS OF MANUFACTURING THE SAME. Two layers of polyimide (KAPTON H, DuPont, Wilmington, Del.) were laminated together to form a mold substrate with a thickness of 250 µm. The mold substrate was laser ablated to form a structured surface with cavities in the shape of the microneedles described below. The structured surface was treated with a seed layer by vapor coating of silver and subsequently electroformed with nickel to form a metallic microneedle array. The thickness of the nickel backplate was approximately 230 µm. The array was removed from the mold and stored prior to use.

The microneedle arrays were elliptical in shape at the base and tapered to a blunt tip with a surface area of approximately 20 µm$^2$. The major axis of the base was approximately 100 µm in length and the minor axis of the base was approximately 65 µm in length. The area of the base was approximately 5105 µm$^2$. The aspect ratio of the microneedles was approximately 3:1. The microneedles were 250 µm tall. The cross-sectional area of a plane aligned with the base, the plane being located at a distance of 0.98 h from the base, was approximately 34 µm. The surface area of the array was 1 cm$^2$, and the tip-to-tip spacing of the microneedles was 400 µm. The microneedles had a channel extending from the base along one side of the shaft and terminating before the tip of the needle.

Human cadaver skin was soaked for approximately one hour in 0.025M phosphate buffer solution (PBS) before being cut to size to fit 5 cm$^2$ Franz cells modified to sit over individual stirrers within an enclosed, temperature-controlled box. The temperature was maintained at 32° C. during the permeation experiment. The receiver cell solution was 0.025M PBS. Impedance measurements were made both before and following microneedle application. Skin samples with a resistivity lower than 10,000 Ω·cm$^2$ were discarded.

The microneedles were attached to the piston of an impactor of the general design shown in FIG. 7 to 10 and applied to the cadaver skin. The piston velocity was 8 m/sec and the piston mass was 7 gm. The needles were then removed and a solution of 0.068 gm/mL sodium alendronate (Onbio Inc, Richmond Hill, Ontario, Canada) in water was applied to the donor side of the Franz cell.

All cells were kept at 32° C. for the duration of the study. Samples were taken from 2 hrs to 168 hrs and analyzed for alendronate concentration by HPLC. Five replicates were performed and average cumulative flux is reported in Table 1. A control sample consisting of the alendronate solution applied to untreated cadaver skin was also tested.

TABLE 1

Alendronate Cumulative Flux [µg/cm$^2$]

| | \multicolumn{7}{c}{Time [hrs]} | | | | | |
|---|---|---|---|---|---|---|
| | 2 | 4 | 6 | 24 | 48 | 72 | 168 |
| treated | 0.30 | 6.5 | 20.7 | 112 | 242 | 388 | 1086 |
| untreated | 0 | 0 | 0 | 0.90 | 3.9 | 8.4 | 21.6 |

Example 2

Following the method of Example 1, a MINITRAN transdermal patch containing 0.0135 gm nitroglycerin (3M, Maplewood, Minn.) was applied to human cadaver skin treated with the microneedles of Example 1. The human cadaver skin was soaked in 0.025M phosphate buffered saline (PBS) and the receptor solution used was also PBS. Five replicates were performed and average cumulative flux is reported in Table 2. A control sample consisting of the transdermal patch applied to untreated cadaver skin was also tested.

TABLE 2

Nitroglycerin Cumulative Flux [µg/cm$^2$]

| | \multicolumn{7}{c}{Time [hrs]} | | | | | |
|---|---|---|---|---|---|---|
| | 0 | 2 | 4 | 6 | 24 | 48 | 72 |
| Treated | 0 | 125 | 286 | 447 | 1899 | 3594 | 4695 |
| Untreated | 0 | 60.7 | 197 | 338 | 1798 | 3507 | 4670 |

Example 3

Following the method of Example 2, a solution of 0.174 gm/mL sodium ceftriaxone (ROCEPHIN, Roche Labs, New Jersey) in water was applied to human cadaver skin treated with the microneedles of Example 1. Average cumulative flux was determined at 2 hours after application of the solution. At subsequent times, the donor solution began decomposing, as indicated by an increasing red color, so no further time points were sampled. The average cumulative flux at 2 hours for the solution applied to treated skin was 46.6 µg/cm$^2$. The average cumulative flux at 2 hours for the solution applied to untreated skin was 0 µg/cm$^2$.

Example 4

Microneedle arrays were prepared according to the method of Example 1. The microneedle arrays were conical in shape and tapered to a blunt tip with a surface area of approximately 20 µm$^2$. The diameter of the base was approximately 42 µm. The area of the base was approximately 1,385 µm$^2$. The aspect ratio of the microneedles was approximately 3:1. The microneedles were 125 µm tall. The cross-sectional area of a plane aligned with the base, the plane being located at a distance of 0.98 h from the base, was approximately 26 µm.

The surface area of the array was 1 cm$^2$, and the tip-to-tip spacing of the microneedles was 300 µm.

Following the method of Example 2, a solution of 0.100 gm/mL LOVENOX (Moudry Apothecary Shop, St. Paul, Minn.) in water was applied to human cadaver skin. Five replicates were performed and average cumulative flux is reported in Table 3. A control sample consisting of the lovenox solution applied to untreated cadaver skin was also tested.

TABLE 3

Lovenox Cumulative Flux [µg/cm$^2$]

| | \multicolumn{8}{c}{Time [hrs]} | | | | | | |
|---|---|---|---|---|---|---|---|---|
| | 4 | 6 | 8 | 10 | 24 | 48 | 72 | 168 |
| treated | 28.3 | 44.3 | 74.9 | 114 | 544 | 1112 | 1642 | 2834 |
| untreated | 0 | 0 | 0 | 0 | 146 | 196 | 203 | 256 |

Example 5

Following the method of Example 4, a solution of 0.100 gm/ml fluorescine isothiocyanate (FITC)-dextran (Sigma Chem Co., St. Louis, Mo.) in water was applied to human cadaver skin treated with the microneedles of Example 4. Average cumulative flux was determined at 2 hours after application of the solution. Three replicates were performed and average cumulative flux is reported in Table 4. A control sample consisting of the FITC-dextran solution applied to untreated cadaver skin was also tested.

TABLE 4

FITC-Dextran Cumulative Flux [µg/cm$^2$]

| | \multicolumn{4}{c}{Time [hrs]} | | | |
|---|---|---|---|---|
| | 6 | 24 | 48 | 72 |
| treated | 66.5 | 387 | 823 | 1271 |
| untreated | 6.4 | 2.2 | 0.8 | 5.0 |

All patents, patent applications, and publications cited herein are each incorporated herein by reference in their entirety, as if individually incorporated by reference. Various modifications and alterations of this invention will become apparent to those skilled in the art without departing from the scope of this invention, and it should be understood that this invention is not to be unduly limited to the illustrative embodiments set forth herein.

The invention claimed is:

1. An article comprising:
   a microneedle device comprising:
      a substrate comprising a first major surface; and
      at least one microneedle projecting from the first major surface of the substrate, the at least one microneedle comprising a base proximate the first major surface of the substrate, wherein the at least one microneedle is tapered from the base to a flat tip distal from the base such that the at least one microneedle comprises a truncated tapered shape;
      wherein the flat tip comprises a surface comprising a surface area measured in a plane aligned with the base of 20 square micrometers or more and 250 square micrometers or less, wherein the surface does not include an opening.

2. An article according to claim 1, wherein the at least one microneedle comprises a plurality of microneedles.

3. An article according to claim 1, wherein the flat tip comprises a surface area of 100 square micrometers or less.

4. An article according to claim 1, wherein the flat tip comprises a surface area of 50 square micrometers or less.

5. An article according to claim 1, wherein the at least one microneedle comprises a height above the first major surface and a maximum base dimension, the height and the maximum base dimension ratio defining an aspect ratio, wherein the aspect ratio is 2:1 or more.

6. An article according to claim 1, wherein the at least one microneedle is fotined of one or more polymers.

7. An article according to claim 1, wherein the base of the at least one microneedle comprises a base area of 900 square micrometers or more.

8. An article comprising:
a microneedle device comprising:
 a substrate comprising a first major surface; and
 a plurality of microneedles projecting from the first major surface of the substrate, each microneedle of the plurality of microneedles comprising a base proximate the first major surface of the substrate, wherein each microneedle of the plurality of microneedles is formed of one or more polymers and is tapered from the base to a flat tip distal from the base such that each microneedle of the plurality of microneedles comprises a truncated tapered shape;
 wherein the flat tip comprises a surface comprising a surface area measured in a plane aligned with the base of 20 square micrometers or more and 100 square micrometers or less, wherein the surface does not include an opening;
 wherein the base of each microneedle of the plurality of microneedles comprises a base area of 900 square micrometers or more;
 and wherein each microneedle of the plurality of microneedles comprises a height above the first major surface and a maximum base dimension, the height and the maximum base dimension ratio defining an aspect ratio, wherein the aspect ratio is 3:1 or more; and a microneedle delivery apparatus capable of accelerating at a velocity of 2m/s or more (a) the microneedle device or (b) a piston that impacts the microneedle device.

9. A method of using a microneedle device article, the method comprising:
 providing an article according to claim 1;
 contacting the skin on a patient with the at least one microneedle;
 forcing the microneedle device against the skin.

10. An article according to claim 1, further comprising a microneedle delivery apparatus capable of accelerating at a velocity of 2 m/s or more (a) the microneedle device or (b) a piston that impacts the microneedle device.

11. An article according to claim 10, wherein the microneedle delivery apparatus further comprises a pressure collar.

12. An article according to claim 10, wherein the microneedle delivery apparatus further comprises a driver operably connected to the piston.

13. A microneedle device comprising:
 a substrate comprising a first major surface; and
 at least one microneedle projecting from the first major surface of the substrate, the at least one microneedle comprising a base proximate the first major surface of the substrate, wherein the at least one microneedle is tapered from the base to a flat tip distal from the base such that the at least one microneedle comprises a truncated tapered shape;
 wherein the flat tip comprises a surface area measured in a plane aligned with the base of 20 square micrometers or more and 250 square micrometers or less.

14. An article according to claim 13, further comprising a microneedle delivery apparatus capable of accelerating at a velocity of 2m/s or more (a) the microneedle device or (b) a piston that impacts the microneedle device.

15. The device according to claim 14, wherein the microneedle delivery apparatus further comprises a pressure collar.

16. An article according to claim 14, wherein the microneedle delivery apparatus further comprises a driver operably connected to the piston.

17. An article according to claim 13, wherein the at least one microneedle comprises a height above the first major surface and a maximum base dimension, the height and the maximum base dimension ratio defining an aspect ratio, wherein the aspect ratio is 2:1 or more.

\* \* \* \* \*

UNITED STATES PATENT AND TRADEMARK OFFICE
CERTIFICATE OF CORRECTION

| | |
|---|---|
| PATENT NO. | : 8,900,194 B2 |
| APPLICATION NO. | : 10/621620 |
| DATED | : December 2, 2014 |
| INVENTOR(S) | : Graham Clarke et al. |

It is certified that error appears in the above-identified patent and that said Letters Patent is hereby corrected as shown below:

On the Title page,

Page 2, Column 2 (Other Publications)
Line 3, Delete "Merrian-Webster" and insert -- Merriam-Webster --, therefor.

In the Claims,

Column 15
Line 16, In Claim 6, delete "fotined" and insert -- formed --, therefor.

Column 16
Line 2, In Claim 8, delete "2m/s" and insert -- 2 m/s --, therefor.

Column 16
Line 33, In Claim 14, delete "2m/s" and insert -- 2 m/s --, therefor.

Signed and Sealed this
Thirtieth Day of June, 2015

Michelle K. Lee
*Director of the United States Patent and Trademark Office*